(12) United States Patent
Pataut et al.

(10) Patent No.: US 6,403,070 B1
(45) Date of Patent: Jun. 11, 2002

(54) ANHYDROUS DEODORANT COMPOSITION

(75) Inventors: Françoise Pataut, Paris; Lionnel Aubert, Asnieres sur Oise, both of (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 09/716,950

(22) Filed: Nov. 22, 2000

(30) Foreign Application Priority Data

Nov. 25, 1999 (FR) .............................. 99 14851

(51) Int. Cl.$^7$ .......................... A61K 7/32; A61K 31/74; A61K 7/00
(52) U.S. Cl. .......................... 424/65; 66/78.03; 66/400; 66/401; 66/DIG. 5
(58) Field of Search .................... 424/65, 66, 78.03, 424/400, 401, DIG. 5

(56) References Cited

U.S. PATENT DOCUMENTS

| | | |
|---|---|---|
| 3,615,972 A | 10/1971 | Morehouse et al. |
| 4,944,937 A | 7/1990 | McCall |
| 5,035,885 A | 7/1991 | Arraudeau et al. |
| 5,221,534 A | 6/1993 | DesLauriers et al. |
| 5,437,860 A | 8/1995 | Jarvis et al. |
| 5,558,872 A | 9/1996 | Jones et al. |
| 5,756,082 A | 5/1998 | Cashin et al. |

FOREIGN PATENT DOCUMENTS

| | | |
|---|---|---|
| EP | 0 056 219 | 7/1982 |
| EP | 0 112 807 | 7/1984 |
| EP | 0 320 473 | 6/1989 |
| EP | 0 348 372 | 12/1989 |
| EP | 0 486 080 | 5/1992 |
| FR | 2 776 187 | 9/1999 |
| JP | 04-9319 | 1/1992 |
| WO | WO 94/12190 | 6/1994 |

OTHER PUBLICATIONS

English language Derwent Abstract of FR 2 776 187.
English language Derwent Abstract of JP 04–9319.

*Primary Examiner*—Shelley A. Dodson
(74) *Attorney, Agent, or Firm*—Finnegan, Henderson, Farabow, Garrett & Dunner, L.L.P.

(57) ABSTRACT

An anhydrous deodorant cosmetic composition comprising (i) at least one deodorant active agent, (ii) at least one block copolymer, (iii) at least one fat-absorbing substance, and (iv) at least one synthetic oil. The at least one block copolymer is chosen from diblock copolymers, triblock copolymers, multiblock copolymers, and radial block copolymers, wherein said at least one block copolymer comprises at least one segment derived from at least one styrene monomer and at least one segment derived from at least one thermoplastic entity chosen from thermoplastic monomers and thermoplastic comonomers

48 Claims, No Drawings

ANHYDROUS DEODORANT COMPOSITION

The present invention relates to an anhydrous deodorant cosmetic composition comprising at least one deodorant active agent, at least one block copolymer, at least one fat-absorbing substance, and at least one synthetic oil.

Many different types of nonaqueous (anhydrous) deodorant compositions have been described in the literature and have appeared on the market in forms such as gels, sticks, creams, roll-ons and aerosols. The solid and semi-solid forms, that is gels, sticks and creams, generally comprise a substance with a liquid base which is solidified or thickened by a consistency agent. These forms of compositions represent one subject of the present invention.

Compositions in a solid form and those in a semi-solid form generally comprise one of:
  (a) a solution of at least one active ingredient in a suitably chosen solvent, (b) a suspension of at least one active ingredient in a nonsolvent medium and (c) a dispersion or emulsion (i) in the continuous phase in which is dispersed a solution of at least one active ingredient, or
  (ii) for which the dissolved at least one active agent constitutes the continuous phase.

There remains, however, a need for a deodorant cosmetic composition having at least one desired property chosen from stability, homogeneity and rheological properties on application. In addition, the composition should not leave a visible, such as a white, residue on the skin either upon application or after application and drying of the composition and/or should leave skin soft to the touch.

The use of at least one gelling agent comprising styrene/elastomer block copolymers in mineral oils has previously been recommended for deodorant sticks in Patent Application WO 94/12190, the disclosure of which is incorporated herein by reference. However, such sticks may leave an undesirable greasy residue on the skin and may not exhibit at least one of the desired advantages mentioned above.

The Inventors have discovered that when an effective amount of at least one fat-absorbing substance and an effective amount of at least one synthetic oil is included with at least one deodorant active agent and at least one block copolymer derived from (i) at least one monomer of styrene and (ii) at least one thermoplastic entity chosen from thermoplastic monomers and thermoplastic comonomers to form a deodorant cosmetic composition, it may be possible to significantly improve the deodorant cosmetic composition and it may be possible to obtain at least one of the above-identified desired properties, such as all of the above-identified desired properties.

By virtue of the present invention it can be possible to obtain stable and homogeneous compositions with a viscosity suitable for a variety of forms (e.g. sticks, gels, and creams) which do not exude and which spread very well over the skin without leaving a visible white and/or greasy residue on application or after drying of the applied deodorant cosmetic composition.

Specifically, one embodiment of the present invention is directed to an anhydrous deodorant cosmetic composition comprising (i) at least one deodorant active agent; (ii) at least one block copolymer chosen from diblock copolymers, triblock copolymers, multiblock copolymers and radial block copolymers, wherein said at least one block copolymer comprises at least one segment derived from at least one styrene monomer and at least one segment derived from at least one thermoplastic entity chosen from thermoplastic monomers and thermoplastic comonomers; (iii) at least one fat-absorbing substance; and (iv) at least one synthetic oil.

Another embodiment of the present invention is directed to an anhydrous deodorant cosmetic composition comprising (i) at least one deodorant active agent in a concentration ranging from 0.1% to 40% by weight relative to the total weight of the composition; (ii) at least one block copolymer chosen from diblock copolymers, triblock copolymers, multiblock copolymers and radial block copolymers, wherein said at least one block copolymer comprises at least one segment derived from at least one styrene monomer and at least one segment derived from at least one thermoplastic entity chosen from thermoplastic monomers and thermoplastic comonomers and wherein said at least one block copolymer is present in a concentration ranging from 0.1% to 7% by weight relative to the total weight of the composition; (iii) at least one fat-absorbing substance in a concentration ranging from 0.1% to 20% relative to the total weight of the composition; and (iv) at least one synthetic oil in a concentration ranging from 5% to 90% relative to the total weight of the composition.

According to the present invention, the term "deodorant active agent" refers to a substance which is capable of at least one of: (1) reducing the flow of sweat and (2) masking, (3) improving and (4) reducing an unpleasant odor resulting from the bacterial decomposition of human sweat.

For example, the at least one deodorant active agent may be chosen from antiperspirant compounds, alum salts, bacteriostatic agents, bactericidal agents (such as, for example, 2,4,4'-trichloro-2'-hydroxydiphenyl ether and 3,7,11-trimethyldodeca-2,5,10-trienol), various zinc salts and odor-absorbing agents (such as sodium bicarbonate and zinc pidolate (zinc pyrrolidonecarboxylate)). Non-limiting examples of antiperspirant compounds include aluminum salts (such as, for example, aluminum chlorohydrate, aluminum hydroxychloride), zirconium salts and aluminum and zirconium salts.

3,7,11-Trimethyldodeca-2,5,10-trienol is, for example, sold under the name Farnesol® by Dragoco and 2,4,4'-trichloro-2'-hydroxydiphenyl ether is sold under the name Irgacare® MP by Ciba-Geigy.

Non-limiting examples of aluminum salts that may be used as the at least one deodorant active agent according to the present invention include aluminum hydroxychloride, sold by Reheis under the name Reach 301 and by Guilini Chemie under the name Aloxicoll PF 40. Non-limiting examples of aluminum and zirconium salts that may be used according to the present invention include the salt sold by the company Reheis under the name Reach A2P-908-SUF.

Complexes of zirconium hydroxychloride and aluminum hydroxychloride and glycine, commonly known under the name "ZAG complexes," may also be used according to the invention.

The diblock copolymers, triblock copolymers, multiblock copolymersand radial block copolymers comprising at least one segment derived from at least one styrene monomer and at least one segment derived from at least one thermoplastic entity chosen from thermoplastic monomers and thermoplastic comonomers which can be used according to the present invention include, for example, those disclosed in U.S. Pat. No. 5,221,534, the disclosure of which is incorporated herein by reference.

For example, the at least one block copolymer may be chosen from those copolymers comprising at least one segment derived from at least one thermoplastic entity chosen from ethylene/$C_3$–$C_4$ alkylene segments, such as hydrogenated copolymers comprising at least one styrene block and at least one ethylene/$C_3$–$C_4$ alkylene block.

According to the present invention, the deodorant cosmetic composition can comprise a blend in mineral oil comprising (i) a hydrogenated copolymer comprising butylene/ethylene blocks and styrene blocks and (ii) a hydrogenated copolymer comprising ethylene/propylene blocks and styrene blocks. For example, a blend comprising, in a concentration ranging from 1% to 20% by weight relative to the total weight of the composition, (i) a hydrogenated copolymer comprising butylene/ethylene blocks and styrene blocks and (ii) a hydrogenated copolymer comprising ethylene/propylene blocks and styrene blocks, and, in a concentration ranging from 80% to 99% by weight relative to the total weight of the composition, mineral oil is within the scope of the present invention.

Such blends of copolymers are sold, for example, by Penreco under the trade names Versagel M200 and Versagel M750 or by Aiglon under the trade names Transgel or Syngel (90% liquid paraffin, 5% butylene/ethylene/styrene hydrogenated copolymer and 5% ethylene/propylene/styrene hydrogenated copolymer).

The at least one fat-absorbing substance which may be used according to the present composition can be chosen from hollow or porous particles with a suitable particle size (as further described below), talcs, starches, starch derivatives, clays, silicas, polyolefins, polystyrenes and teflons.

Non-limiting examples of starch derivatives include the esterified maize starch sold under the trade name Dryflo Plus by National Starch and the non-pregelatinized hydroxypropylated potato distarch phosphate sold under the trade name Farinex VA-100 by Avebe. Non-limiting examples of silicas include porous silica microspheres sold under the trade name Silica Bead SB-700 by Miyoshi and the hydrophobic pyrogenic silica sold under the trade name Aerosil R972 by Degussa. A non-limiting example of clays is the green clay sold under the trade name Gamma 2 KGY by Bentofrance. A non-limiting example of polyethylenes is the polyethylene powder sold under the trade name Acumist B6 by Allied Chemical.

The hollow particles which may be used in the deodorant cosmetic compositions according to the present invention have a mean particle size (such as a diameter or characteristic axis) generally ranging from 5 µm to 200 µm, such as from 10 µm to 100 µm and further such as from 15 µm to 60 µm.

The particles may comprise thermoplastic materials, such as polyamides (such as nylon) and polymers and copolymers derived from at least one monomer chosen from acrylonitrile, vinylidene chloride, vinyl chloride, acrylic and styrene, wherein the polymers and copolymers may optionally be expanded. Non-limiting examples of acrylic monomers are methyl acrylate, ethyl acrylate and methacrylate. Non-limiting examples of styrene monomers are α-methylstyrene and styrene. A non-limiting example of nylon particles is the "Orgasol" particles sold by Atochem, which are porous solid spheres with a diameter ranging from 5 µm to 60 µm.

In one embodiment, the particles are hollow particles comprising at least one material chosen from expanded copolymers derived from of (i) vinylidene chloride and (ii) acrylonitrile and expanded terpolymers derived from (i) vinylidene chloride, (ii) acrylonitrile and (iii) methacrylate. For example, the hollow particles can comprise at least one polymer comprising: units derived from vinylidene chloride in a concentration ranging up to 60% by weight relative to the total weight of said polymer, units derived from acrylonitrile in a concentration ranging from 20% to 90% by weight relative to the total weight of said polymer and units derived from a monomer chosen from acrylic monomers and styrene monomers in a concentration ranging from up to 50% by weight relative to the total weight of said polymer, wherein the sum of percentages is equal to 100. These particles can be dry or hydrated and may be chosen from, for example, those sold under the trade name Expancel by Nobel Casco, such as those sold under the references 551 DE (particle size of approximately 50 µm and density of approximately 35 kg/m$^3$), 551 DE 12 (particle size of approximately 12 µm and density of approximately 40 kg/m$^3$), 551 DE 20 (particle size of approximately 30 µm and density of approximately 65 kg/m$^3$), 551 DE 50 (particle size of approximately 40 µm), 461 DE 50 and 642 WE 50 (particle size of approximately 50 µm) and 551 DE 80 (particle size of approximately 80 µm). Further, according to the present invention, the aforementioned expanded polymer may, for example, form particles having a particle size of approximately 18 µm and a density of approximately 60 to approximately 90 kg/m$^3$ and particles having a particle size of approximately 34 µm and a density of approximately 20 kg/m$^3$.

Useful particles may also comprise at least one material chosen from nonexpanded copolymers derived from (i) vinylidene chloride and (ii) acrylonitrile and nonexpanded terpolymers derived from (i) vinylidene chloride, (ii) acrylonitrile and (iii) methacrylate, such as, for example, those sold under the trade name Expancel with the reference 551 DU 10 (particle size of approximately 10 µm) and 461 DU 15 (particle size of approximately 15 µm).

Other polymeric hollow particles which can be used according to the present invention may comprise at least one material chosen from polymers and copolymers derived from esters (such as, for example, vinyl acetate and vinyl lactate) and acids (such as, for example, itaconic acid, citraconic acid, maleic acid and fumaric acid). See, for example, JP 4009319, the disclosure of which are incorporated herein by reference.

In another embodiment of the present invention, the particles are provided in the form of beads, fibers or needles.

The particles sold under the trade name Expancel can be obtained, for example, according to the processes of Patents and Patent Applications EP-56 219, EP-348 372, EP-486 080, EP-320 473, EP-112 807, and U.S. Pat. No. 3,615,972, the disclosures of which are incorporated herein by reference. The internal cavity of the particles may comprise at least one gas, such as air, nitrogen and at least one hydrocarbon (such as isobutane and isopentane).

Yet another embodiment of the present invention is directed to an anhydrous deodorant cosmetic composition comprising:

(a) at least one deodorant active agent in a concentration ranging from 0.1% to 40% by weight relative to the total weight of the composition, (b) at least one block copolymer chosen from diblock copolymers, triblock copolymers, multiblock copolymers and radial block copolymers, wherein said at least one block copolymer comprises at least one segment derived from at least one styrene monomer and at least one segment derived from at least one thermoplastic entity chosen from thermoplastic monomers and thermoplastic comonomers and wherein said at least one block copolymer is present in a concentration ranging from 0.1% to 7% by weight relative to the total weight of the composition, (c) at least one hollow particle comprising at least one expanded terpolymer derived from (i) vinylidene chloride, (ii) acrylonitrile and (iii) methacrylate, wherein said at least one hollow particle is present in a concentration ranging from 0.1% to 10% by weight relative to the total weight of the composition, such as from 0.1% to 5%, and (d) at least one synthetic oil in a concentration ranging from 5% to 90% by weight relative to the total weight of the composition.

For example, the at least one synthetic oil which can be used according to the present invention can be chosen from isoparaffins of formula (I):

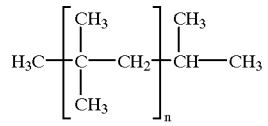

wherein n≧2, such as ranging from 2 to 40. Non-limiting examples of the at least one synthetic oil include isohexadecane wherein n=3, and isododecane wherein n=2. Such synthetic oils wherein n is equal to 2,3,4, 16 or 38 include the products sold under the names Permethyl 99A, 101A, 102A, 104A or 106A by Preperse Inc. and the product Arlamol HD, sold by ICI, corresponding to the formula (I) wherein n is equal to 3.

In the inventive deodorant cosmetic compositions, the at least one deodorant active agent is present in a concentration generally ranging from about 0.1% to about 40% by weight relative to the total weight of the composition, such as from about 0.5% to about 25%. The at least one block copolymer is present in a concentration generally ranging from about 0.1% to about 7% by weight relative to the total weight of the composition, such as from about 2 to about 5%. The at least one fat-absorbing substance is present in a concentration generally ranging from about 0.1% to about 20% by weight relative to the total weight of the composition, such as from about 0.5% to about 10%. The at least one synthetic oil is present in a concentration generally ranging from about 5% to about 90% by weight relative to the total weight of the composition, such as from about 20% to about 60%.

The deodorant cosmetic composition according to the present invention can further comprise at least one consistency agent. The at least one consistency agent may be chosen from, for example, paraffin waxes, stearyl alcohols, waxes of natural origin (such as microcrystalline waxes, ceresin, ozokerite, candelilla wax, carnauba wax, hydrogenated castor oil, hydrogenated palm oil and hydrogenated coconut oil) and polyethylene waxes (such as those disclosed in French Patent No. 2,776,187, the disclosure of which is incorporated herein by reference, and further such as mixtures of natural waxes and polyethylene waxes all having a melting point of greater than 80° C, such as those disclosed in the above cited French patent).

If present, the at least one consistency agent is generally present in the composition in an amount sufficient to yield a desired form for the composition, such as a gel, a cream or a stick.

The deodorant cosmetic composition according to the present invention can further comprise at least one suitable additive such as those known in the field of deodorant cosmetic products. Non-limiting examples of the at least one suitable additive include soothing agents, fragrances, preservatives, antioxidants, sequestering agents, suspending agents (such as bentonites and hectorites) and emollients (such as fatty acid esters, such as, for example, isopropyl myristate and isopropyl palmitate).

The deodorant cosmetic composition according to the present invention may be pressurized and may optionally be packaged as an aerosol. In one embodiment, the inventive composition may further comprise at least one propellant such as those generally used in products of this and similar type, which are well-known to a person skilled in the art. Non-limiting examples of the at least one propellant include volatile hydrocarbons (such as n-butane, propane, isobutane and mixtures thereof, optionally with at least one hydrocarbon chosen from chlorinated hydrocarbons and fluorinated hydrocarbons). For example, the at least one propellant may be chosen from compounds sold by Dupont de Nemours under the names Freon® and Dymel® such as monofluorotrichloromethane, difluorodichloromethane, tetrafluorodichloroethane and 1,1-difluoroethane, sold, for example, under the trade name Dymel 152 A by Dupont.

The at least one propellant for the aerosol may also be chosen from carbon dioxide, nitrous oxide, nitrogen and compressed air.

If present in the deodorant cosmetic composition according to the present invention, the at least one propellant is present in a concentration ranging from 20% to 85% by weight relative to the total weight of the composition.

Needless to say, a person skilled in the art will take care to select the possible additional compound(s) mentioned above such that the advantageous properties of the deodorant cosmetic composition according to the present invention are not, or are not substantially, adversely affected by the envisaged addition(s).

Other embodiments of the present invention relate to a cosmetic process for reducing the flow of sweat, and/or masking, improving or reducing the unpleasant smell resulting from the bacterial decomposition of human sweat, and to a process for treating human axillary smells, which comprises applying, to the axillary surface, an effective amount of a composition as described above.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result. The percentages are given on a weight basis.

EXAMPLE 1

An anhydrous antiperspirant cream was prepared with the following composition: (amounts expressed in grams)

| | |
|---|---|
| Versagel M 200, sold by Penreco | 25 |
| Micronized anhydrous aluminum hydroxychloride | 25 |
| Hydroxypropylated potato distarch phosphate (Farinex VA-100 from Avebe) | 5 |
| Expanded microspheres of vinylidene chloride/acrylonitrile/methyl methacrylate copolymer comprising isobutane, sold under the trade name Expancel 551 DE 20 by Nobel Casco | 1 |
| Isohexadecane | 10 |
| Isododecane | 28.95 |
| Di-tert-butyl-4-hydroxytoluene | 0.05 |
| Hydrogenated castor oil | 5 |

The hydrogenated castor oil was introduced into a manufacturing vessel, which was then heated to 95–100° C. with stirring.

A premix of Versagel M200, isohexadecane, and isododecane was subsequently introduced therein, followed by the di-tert-butyl-4-hydroxytoluene. After complete melting and homogenization, the mixture was cooled to 80° C. The micronized anhydrous aluminum hydroxychloride, the distarch phosphate, and the Expancel were then added. The mixture was vigorously stirred with a turbine and then the temperature was reduced to 50° C.

EXAMPLE 2

An anhydrous antiperspirant stick was prepared with the following composition: (amounts expressed in grams)

| | |
|---|---|
| Versagel M 200, sold by Penreco | 25 |
| Micronized anhydrous aluminum hydroxychloride | 25 |
| Hydroxypropylated potato distarch phosphate (Farinex VA-100 from Avebe) | 5 |
| Expanded microspheres of vinylidene chloride/acrylonitrile/methyl methacrylate copolymer comprising isobutane, sold under the trade name Expancel 551 DE 20 by Nobel Casco | 1 |
| Isohexadecane | 10 |
| Isododecane | 13.95 |
| Di-tert-butyl-4-hydroxytoluene | 0.05 |
| Hydrogenated castor oil | 5 |
| Stearyl alcohol | 15 |

The hydrogenated castor oil and the stearyl alcohol were introduced into a manufacturing vessel, which was then heated to 95-100° C. with stirring.

A premix of Versagel M200, isohexadecane, and isododecane was subsequently introduced therein, following by the di-tert-butyl-4-hydroxytoluene. After complete melting and homogenization, the mixture was cooled to 80° C. The micronized anhydrous aluminum hydroxychloride, the distarch phosphate and the Expancel were then added. The mixture was vigorously stirred with a turbine and then the temperature was reduced to 65° C.

EXAMPLE 3

An anhydrous antiperspirant aerosol was prepared with the following composition: (amounts expressed in grams)

| | |
|---|---|
| DISPENSABLE | |
| Versagel M 200, sold by Penreco | 5 |
| Isohexadecane | 6 |
| Isododecane | 5 |
| Micronized anhydrous aluminum hydroxychloride | 3 |
| Expanded microspheres of vinylidene chloride/acrylonitrile/methyl methacrylate copolymer comprising isobutane, sold under the trade name Expancel 551 DE 20 by Nobel Casco | 0.5 |
| Bentonite (Bentone 38V from Rheox) | 0.5 |
| PROPELLANT | |
| Isobutane | 80 |

Other embodiments of the invention will be apparent to those skilled in the art from consideration of the specification and practice of the invention disclosed herein. It is intended that the specification and examples be considered as exemplary only.

What is claimed is:

1. An anhydrous deodorant cosmetic composition comprising:
   (i) at least one deodorant active agent,
   (ii) at least one block copolymer chosen from diblock copolymers, triblock copolymers, multiblock copolymers, and radial block copolymers, wherein said at least one block copolymer comprises at least one segment derived from at least one styrene monomer and at least one segment derived from at least one thermoplastic entity chosen from thermoplastic monomers and thermoplastic comonomers,
   (iii) at least one fat-absorbing substance, and
   (iv) at least one synthetic oil.

2. An anhydrous deodorant cosmetic composition comprising:
   (i) at least one deodorant active agent in a concentration ranging from 0.1% to 40% by weight relative to the total weight of the composition;
   (ii) at least one block copolymer chosen from diblock copolymers, triblock copolymers, multiblock copolymers and radial block copolymers, wherein said at least one block copolymer comprises at least one segment derived from at least one styrene monomer and at least one segment derived from at least one thermoplastic entity chosen from thermoplastic monomers and thermoplastic comonomers and wherein said at least one block copolymer is present in a concentration ranging from 0.1% to 7% by weight relative to the total weight of the composition;
   (iii) at least one fat-absorbing substance in a concentration ranging from 0.1% to 20% relative to the total weight of the composition; and
   (iv) at least one synthetic oil in a concentration ranging from 5% to 90% relative to the total weight of the composition.

3. The composition according to claim 1, wherein said at least one deodorant active agent is present in a concentration ranging from 0.1% to 40% by weight relative to the total weight of the composition.

4. The composition according to claim 1, wherein the at least one block copolymer is present in an amount ranging from 0.1% to 7% by weight relative to the total weight of the composition.

5. The composition according to claim 1, wherein the at least one fat-absorbing substance is present in an amount ranging from 0.1% to 20% by weight relative to the total weight of the composition.

6. The composition according to claim 1, wherein the at least one at least one synthetic oil is present in an amount ranging from 5% to 90% by weight relative to the total weight of the composition.

7. The composition according to claim 1, wherein said at least one fat-absorbing substance is chosen from hollow particles having a mean particle size ranging from 1 µm to 300 µm.

8. The composition according to claim 3, wherein the hollow particles have a mean particle size ranging from 1 µm to 150 µm.

9. The composition according to claim 8, wherein the hollow particles have a mean particle size ranging from 10 µm to 100 µm.

10. The composition according to claim 8, wherein the hollow particles have a mean particle size ranging from 15 µm to 60 µm.

11. The composition according to claim 7, wherein the hollow particles are chosen from beads, fibers, and needles.

12. The composition according to claim 7, wherein the hollow particles comprise at least one thermoplastic material.

13. The composition according to claim 7, wherein the hollow particles comprise at least one material chosen from nylon and polymers and copolymers derived from at least one monomer chosen from vinylidene chloride, acrylonitrile, acrylic, and styrene monomers.

14. The composition according to claim 7, wherein the hollow particles comprise at least one material chosen from expanded polymers derived from at least one monomer chosen from vinylidene chloride, acrylonitrile, acrylic, and styrene and copolymers derived from at least one monomer chosen from vinylidene chloride, acrylonitrile, acrylic, and styrene.

15. An anhydrous deodorant composition comprising:
   (a) at least one deodorant active agent in a concentration ranging from 0.1% to 40% by weight relative to the total weight of the composition,
   (b) at least one block copolymer chosen from diblock copolymers, triblock copolymers, multiblock copolymers and radial block copolymers, wherein said at least one block copolymer comprises at least one segment derived from at least one styrene monomer and at least one segment derived from at least one thermoplastic entity chosen from thermoplastic monomers and thermoplastic comonomers, and wherein said at least one block copolymer is present in a concentration ranging from 0.1% to 7% by weight relative to the total weight of the composition,
   (c) hollow particles having a mean particle size ranging from 1 µm to 300 µm in a concentration ranging from 0.1 to 10% by weight relative to the total weight of the composition; and
   (d) at least one synthetic oil in a concentration ranging from 5 to 90% by weight relative to the total weight of the composition.

16. The composition according to claim 15, wherein the hollow particles have a mean particle size ranging from 1 µm to 150 µm.

17. The composition according to claim 15, wherein the hollow particles have a mean particle size ranging from 10 µm to 100 µm.

18. The composition according to claim 15, wherein the hollow particles have a mean particle size ranging from 15 µm to 60 µm.

19. The composition according to claim 15, wherein the hollow particles are chosen from beads, fibers, and needles.

20. The composition according to claim 15, wherein the hollow particles comprise at least one thermoplastic material.

21. The composition according to claim 15, wherein the hollow particles comprise at least one material chosen from nylon and polymers and copolymers derived from at least one monomer chosen from vinylidene chloride, acrylonitrile, acrylic, and styrene monomer.

22. An anhydrous deodorant composition comprising:
   (a) at least one deodorant active agent in a concentration ranging from 0.1% to 40% by weight relative to the total weight of the composition,
   (b) at least one block copolymer chosen from diblock copolymers, triblock copolymers, multiblock copolymers and radial block copolymers, wherein said at least one block copolymer comprises at least one segment derived from at least one styrene monomer and at least one segment derived from at least one thermoplastic entity chosen from thermoplastic monomers and thermoplastic comonomers and wherein said at least one block copolymer is present in a concentration ranging from 0.1% to 7% by weight relative to the total weight of the composition,
   (c) at least one hollow particle comprising at least one expanded terpolymer derived from (i) vinylidene chloride, (ii) acrylonitrile and (iii) methacrylate, wherein said at least one hollow particle is present in a concentration ranging from 0.1 to 5% by weight relative to the total weight of the composition, and
   (d) at least one synthetic oil in a concentration ranging from 5 to 90% by weight relative to the total weight of the composition.

23. The composition according to claim 1, wherein the at least one fat-absorbing substance is chosen from talcs, starches, starch derivatives, clays, silicas, polyolefins, polystyrenes and teflons.

24. The composition according to any claim 1, wherein the at least one synthetic oil is chosen from isoparaffins of formula (I):

$$H_3C \left[\begin{array}{c} CH_3 \\ | \\ C-CH_2 \\ | \\ CH_3 \end{array}\right]_n \begin{array}{c} CH_3 \\ | \\ CH-CH_3 \end{array} \quad (I)$$

wherein $n \geq 2$.

25. The composition according to claim 24, wherein n ranges from 2 to 40.

26. The composition according to claim 24, wherein n=3 and the least one synthetic oil is isohexadecane.

27. The composition according to claim 24, wherein n=2 and the synthetic oil is isododecane.

28. The composition according to claim 1, wherein the at least one segment derived from at least one thermoplastic entity is chosen from ethylene/$C_3$–$C_4$ alkylene segments.

29. The composition according to claim 28, wherein the at least one block copolymer is chosen from hydrogenated block copolymers comprising at least one styrene block and at least one ethylene/$C_3$–$C_4$ alkylene block.

30. The composition according to claim 29, wherein the at least one block copolymer comprises a blend in mineral oil of (i) at least one hydrogenated copolymer comprising at least one butylene/ethylene block and at least one styrene block and (ii) at least one hydrogenated copolymer comprising at least one ethylene/propylene block and at least one styrene block.

31. The composition according to claim 30, wherein the blend comprises hydrogentated copolymers in a concentration ranging from 1 to 20% by weight relative to the total weight of the blend, and mineral oil in a concentration ranging from from 80% to 99% by weight relative to the total weight of the blend.

32. The composition according to claim 1, further comprising at least one consistency agent.

33. The composition according to claim 32, wherein the at least one consistency agent is present in an amount sufficient to yield a desired form for the composition.

34. The composition according to claim 32, wherein the desired form is chosen from gel, cream, and stick forms.

35. The composition according to claim 32, wherein the at least one consistency agent is hydrogenated castor oil.

36. The composition according to claim 32, wherein the at least one consistency agent is chosen from paraffin waxes, stearyl alcohols, waxes of natural origin and polyethylene waxes.

37. The composition according to claim 1, further comprising at least one suitable additive chosen from soothing agents, fragrances, preservatives, antioxidants, sequestering agents, suspending agents and emollients.

38. The composition according to claim 37, wherein said at least one suitable additive is chosen from suspending agents and wherein said composition is in the form of an aerosol.

39. The composition according to claim 1, further comprising at least one propellant.

40. The composition according to claim 1, wherein said composition is in the form of an aerosol.

41. The composition according to claim 1, wherein the at least one deodorant agent is chosen from alum salts, bacteriostatic agents, bactericidal agents, zinc salts and odor-absorbing agents.

42. The composition according to claim 41, wherein the at least one deodorant active agent is chosen from bactericidal agents and odor absorbers.

43. The composition according to claim 1, wherein the at least one deodorant active agent is chosen from antiperspirants.

44. The composition according to claim 1, wherein the at least one deodorant active agent is an antiperspirant agent chosen from aluminum salts, zirconium salts, aluminum and zirconium salts and complexes of zirconium hydroxychloride, aluminum hydroxychloride and glycine.

45. The composition according to claim 44, wherein the at least one antiperspirant agent is aluminum hydroxychloride.

46. A method for reducing a flow of sweat, comprising applying to a human body an effective amount of a composition comprising at least one deodorant active agent, at least one block copolymer, at least one fat-absorbing substance and at least one synthetic oil, wherein:

said at least one block copolymer is chosen from diblock copolymers, triblock copolymers, multiblock copolymers, and radial block copolymers, wherein said at least one block copolymer comprises at least one segment derived from at least one styrene monomer and at least one segment derived from at least one thermoplastic entity chosen from thermoplastic monomers and thermoplastic comonomers.

47. A method for treating human axillary odor comprising applying to a human axillary surface an effective amount of a composition comprising at least one deodorant active agent, at least one block copolymer, at least one fat-absorbing substance, and at least one synthetic oil, wherein:

said at least one block copolymer is chosen from diblock copolymers, triblock copolymers, multiblock copolymers, and radial block copolymers, wherein said at least one block copolymer comprises at least one segment derived from at least one styrene monomer and at least one segment derived from at least one thermoplastic entity chosen from thermoplastic monomers and thermoplastic comonomers.

48. A method for masking, improving or reducing an unpleasant smell resulting from bacterial decomposition of human sweat comprising applying to a human body an effective amount of a composition comprising at least one deodorant active agent, at least one block copolymer, at least one fat-absorbing substance and at least one synthetic oil, wherein:

said at least one block copolymer is chosen from diblock copolymers, triblock copolymers, multiblock copolymers, and radial block copolymers, wherein said at least one block copolymer comprises at least one segment derived from at least one styrene monomer and at least one segment derived from at least one thermoplastic entity chosen from thermoplastic monomers and thermoplastic comonomers.

* * * * *